(12) United States Patent
Parakka et al.

(10) Patent No.: US 8,153,728 B2
(45) Date of Patent: Apr. 10, 2012

(54) PDMS-PVP BLOCK COPOLYMERS

(75) Inventors: James Parakka, San Bruno, CA (US);
Keith R. McCrea, Concord, CA (US);
Robert S. Ward, Berkeley, CA (US)

(73) Assignee: DSM IP Assets B.V., Heerlen (NL)

( * ) Notice: Subject to any disclaimer, the term of this patent is extended or adjusted under 35 U.S.C. 154(b) by 106 days.

(21) Appl. No.: 12/531,200

(22) PCT Filed: Mar. 13, 2008

(86) PCT No.: PCT/US2008/056825
§ 371 (c)(1),
(2), (4) Date: Dec. 14, 2009

(87) PCT Pub. No.: WO2008/112874
PCT Pub. Date: Sep. 18, 2008

(65) Prior Publication Data
US 2010/0099829 A1    Apr. 22, 2010

Related U.S. Application Data

(60) Provisional application No. 60/895,042, filed on Mar. 15, 2007.

(51) Int. Cl.
C08F 30/08    (2006.01)
C08F 293/00   (2006.01)

(52) U.S. Cl. ......... 525/100; 525/421; 525/451; 526/263

(58) Field of Classification Search .................. 525/100, 525/421, 451; 526/263
See application file for complete search history.

(56) References Cited

U.S. PATENT DOCUMENTS

| | | | |
|---|---|---|---|
| 5,135,297 A | 8/1992 | Valint, Jr. | |
| 5,449,729 A | 9/1995 | Lai | |
| 5,973,075 A | 10/1999 | Gagné et al. | |
| 6,555,619 B1 | 4/2003 | Kennedy et al. | |
| 2003/0195136 A1 | 10/2003 | Carswell et al. | |
| 2004/0142016 A1 | 7/2004 | Luthra et al. | |
| 2006/0074208 A1* | 4/2006 | Laredo | 526/279 |
| 2006/0147492 A1 | 7/2006 | Hunter et al. | |

FOREIGN PATENT DOCUMENTS

| | | |
|---|---|---|
| JP | 2000-053716 A | 2/2000 |
| WO | WO-2006/039467 A2 | 4/2006 |

OTHER PUBLICATIONS

Feng et al. (One-Step Method for Synthesis of PDMS-Based Macroazoinitiators and Block Copolymers from the Initiators, Macromolecular Chemistry and Physics, 2006, 207, 1575-1583; published on line Aug. 24, 2006).*

Bertolucci, Massimo et al., "Wetting behavior of films of new fluorinated styrene-siloxane block copolymers," Macromolecules, 2004, vol. 34, No. 10, pp. 3666-3672.

Pinteala, Mariana et al., "Concentration- and pH-dependent conformational changes and aggregation of block copolymers of poly(methacrylic acid) and poly(dimethylsiloxane) in aqueous media, based on fluorescence spectra of pyrene and potentiometry," Macromolecules, 2004, vol. 37, No. 12, pp. 4623-4634.

* cited by examiner

*Primary Examiner* — Ling Choi
*Assistant Examiner* — Chun-Cheng Wang
(74) *Attorney, Agent, or Firm* — Birch, Stewart, Kolasch & Birch, LLP

(57) ABSTRACT

Methods for preparing functionalized polyvinylpyrrolidones with polymerizable functions. Also, amphipathic polydimethylsiloxane-PVP block copolymers, such as

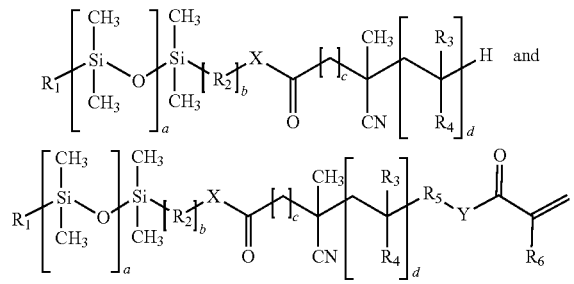

and (meth)acrylated and (meth)acrylamide-functionalized polyvinylpyrrolidone compounds, such as

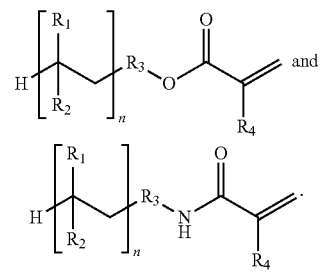

The block copolymers are useful as biomaterial components in biomedical devices. They provide improved wettability, lubricity, and material compatibility to the biomedical device, e.g., ophthalmic lenses.

9 Claims, No Drawings

PDMS-PVP BLOCK COPOLYMERS

This application is the National Phase of PCT/US2008/056825, filed on Mar. 13, 2008, which claims priority under 35 U.S.C. 119(e) to U.S. Provisional Application No. 60/895,042 filed on Mar. 15, 2007. The foregoing are hereby expressly incorporated by reference into the present application.

FIELD OF THE INVENTION

This invention relates to polymerizable poly(N-vinyl-2-pyrrolidone) (PVP) and amphipathic copolymers containing polydimethylsiloxane (PDMS) and polyvinylpyrrolidone. Such copolymers are of particular use as components in biomedical devices such as ophthalmic applications and wound care.

BACKGROUND OF THE INVENTION

N-vinyl-2-pyrrolidone and its polymer, poly(N-vinyl-2-pyrrolidone) (PVP), is a water soluble and biocompatible polymer that has been widely used for a range of commercial applications including for tablet binding, hair fixation, wetting agents in ophthalmic lens formulations, membranes, adhesives, hydrophilic coatings, etc. Several methods for preparation of functionalized polyvinylpyrrolidones have been reported, for instance using azo radical initiators in the presence of chain transfer agents (e.g., mercaptoethanol, isopropanol, isopropoxyethanol, mercaptoethylamine, mercaptopropionic acid). See e.g. U.S. Pat. No. 5,135,297 (SURFACE COATING OF POLYMER OBJECTS); U.S. Pat. No. 6,756,449 B2 (AND BLOCK COPOLYMERS CONTAINING POLY (VINYL PYRROLIDONE) UNITS, MEDICAL DEVICES, AND METHODS); and US 2005/0119404 A1 (PROCESS FOR THE PREPARATION OF AMPHIPHILIC POLY (N-VINYL-2-PYRROLIDONE) BLOCK COPOLYMERS). The disclosure of each of these documents is included herein by reference.

It is desirable in some cases to build functionality into the PVP to prepare materials that will be retained permanently in the final functional polymer device without leaching of the PVP component during use. For instance, (meth)acrylated or (meth)acrylamide functionalized PVP derivatives will find utility in contact lens compositions. In practice, during irradiation or thermal polymerization of the contact lens mix, the functional PVP will be covalently bonded into the crosslinked network and provide a non-leachable wettable ophthalmic lens.

Copolymers that incorporate silicone (PDMS) blocks and hydrophilic moieties such as PVP, poly(dialkylacrylamide) (e.g. polydimethylacrylamide, polyN-isopropylacrylamide and the like), and polyalkyleneglycol should compatibilize the hydrophobic and hydrophilic components of a contact lens formulation generating optically clear and functional lenses. These copolymers would be useful as active components in applications such as silicone hydrogel lenses. In addition, amphiphilic moieties will also find use in lens care solutions targeted for specific types of contact lens. Besides ophthalmic and lens care solutions, other applications for the amphipathic block copolymers include use in tissue engineering, transdermal implants and wound dressings, industrial adhesives, sealants, surface protecting agents, drug release agents and other biomedical applications.

SUMMARY OF THE INVENTION

The present invention discloses methods for preparation of functionalized polyvinylpyrrolidone (PVP) with polymerizable functions and also of novel amphipathic polydimethylsiloxane—PVP copolymers. The block copolymers of the present invention are particularly useful as biomaterial components in biomedical devices. Preferred embodiments of materials disclosed in this invention provide improved wettability, lubricity, and material compatibility to the biomedical device (e.g. an ophthalmic lens).

One generic embodiment of this invention is an amphipathic diblock copolymer compound having the following structure:

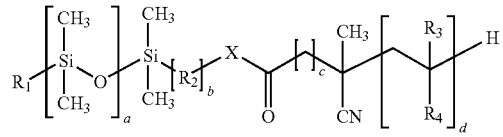

$R_1$ = alkyl, alkoxy; $R_2$ = $(CH2)n$; $(CH2)m$—$O(CH2)n$, m and n can be between 1-16;
a = 1-200; b = 1-6; c = 1-6; d = 1-10000; X = O, NH, S; $R_3$ = H, CH3;
$R_4$ = pyrrolidinone, $C(=O)OH$, $C(=O)OAlkyl$, Ph, substituted Ph,
$C(=O)NH2$, $C(=O)N(alkyl)2$, $OC(=O)CH3$, OH,
$C(=O)$-oxylethylphosphorycholine In typical specific embodiments of that diblock copolymer, $R_1$ is butyl, "a" ranges from 2 to 50, $R_2$ is $(CH_2)_3$ or $(CH_2)_3$—O—$(CH_2)_2$, "b" is 1, X is O or NH, $R_3$ is H, $R_4$ is pyrrolidinone, and "d" ranges from 10 to 10,000. These novel amphipathic diblock copolymers may be formulated for use: as a lens care component for contact lenses, e.g., silicone hydrogel lenses; as an oxygen permeable and wettable backing material for a wound healing device; as a scaffold for tissue engineering; or as a component for controlled drug release.

Another generic embodiment of this invention is an amphipathic triblock copolymer compound having the following structure:

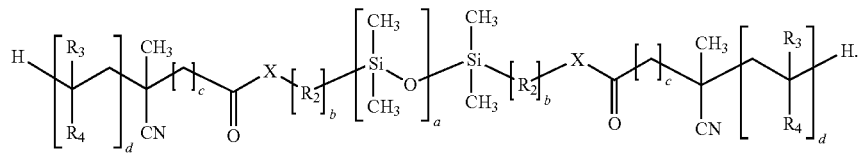

$R_2$ = $(CH2)n$; $(CH2)m$—$O(CH2)n$, m and n can be between 1-16;
a = 1-200; b = 1-6; c = 1-6; d = 1-10000; X = O, NH, S, $R_3$ = H, CH3; $R_4$ = pyrrolidinone,
$C(=O)OH$, $C(=O)OAlkyl$, Ph, substituted Ph, $C(=O)NH2$, $C(=O)N(alkyl)2$,
$OC(=O)CH3$, OH, $C(=O)$-oxylethylphosphorycholine In typical specific embodiments of that triblock copolymer, $R_2$ is $(CH_2)_3$ or $(CH_2)_3$—O—$(CH_2)_2$, $R_3$ is H, $R_4$ is pyrrolidinone, X is O or NH, "a" ranges from 2 to 50, "b" is 1, "c" is 2, and "d" ranges from 10 to 10,000. These novel amphipathic triblock copolymers may be formulated for use: as a lens care component for contact lenses, e.g., silicone hydrogel lenses; as an oxygen permeable and wettable backing material for a wound healing device; as a scaffold for tissue engineering; or as a component for controlled drug release.

Yet another generic embodiment of the present invention is an amphipathic diblock copolymer compound bearing polymerizable functionality, and having this structure:

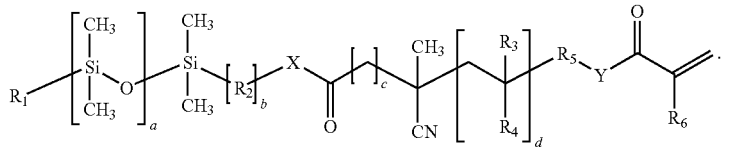

$R_2 = (CH_2)n$; $(CH_2)m—O(CH_2)n$, m and n can be between 1-16;
a = 1-200; b = 1-6; c = 1-6; d = 1-10000; X = O, NH, S; Y = O, NH;
$R_3$ = H, CH3; $R_4$ = pyrrolidinone, C(═O)OH, C(═O)OAlkyl, Ph, substituted Ph, C(═O)NH2, C(═O)N(alkyl)2, OC(═O)CH3, OH, C(═O)-oxylethylphosphorycholine;
$R_5$ = C(CH3)2—O—CH2—CH2, C(CH3)2, S—(CH2)2, C(CH3)2—O—C(═O)—NH—(CH2)2, C(CH3)2—O—CH2—CH2—O—C(═O)—NH—(CH2)2, S—(CH2)2—O—C(═O)—NH—(CH2)2;
$R_6$ = H or CH3

In typical specific embodiments of that diblock copolymer, $R_1$ is butyl, "a" ranges from 2 to 50, $R_2$ is $(CH_2)_3$ or $(CH_2)_3$—O—$(CH_2)_2$, "b" is 1, X is O or NH, $R_3$ is H, $R_4$ is pyrrolidinone, "d" ranges from 10 to 10,000, $R_5$ is $C(CH_3)_2$—O—$CH_2$—$CH_2$ or $C(CH_3)$, Y is O or NH, and $R_6$ is $CH_3$. These novel amphipathic diblock copolymers may be formulated for use: as a lens care component for silicone hydrogel contact lenses; as an oxygen permeable and wettable backing material for a wound healing device; as a scaffold for tissue engineering; or as a component for controlled drug release.

This invention also provides a (meth)acrylated polyvinylpyrrolidone compound of the general structure depicted below.

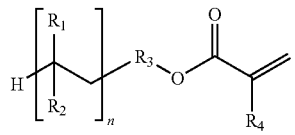

wherein $R_1$ is hydrogen or $C_{1-8}$-alkyl, preferably H; $R_2$ is pyrrolidinone; n=1–10,000; $R_3$ is a divalent aliphatic linkage chain containing up to 8 carbon atoms and up to 2 oxygen, sulfur, and/or nitrogen atoms in the linkage chain, such as $C(CH_3)_2$—$CH_2$—$CH_2$, $C(CH_3)_2$, S—$(CH_2)_2$, $C(CH_3)_2$—O—C(═O)—NH—$(CH_2)_2$, $C(CH_3)_2$—$CH_2$—$CH_2$—O—C(═O)—NH—$(CH_2)_2$, or S—$(CH_2)_2$—O—C(═O)—NH—$(CH_2)_2$; and $R_4$ is hydrogen or $C_{1-8}$-alkyl, such as $CH_3$. In specific embodiments: $R_1$=H, $R_3$=C$(CH_3)_2$—O—$CH_2$—$CH_2$, $R_4$=$CH_3$, and n=10–1000; or $R_1$=H, $R_3$=C$(CH_3)_2$, $R_4$=H, and n=10–1000, or $R_1$=H, $R_3$=S—$(CH_2)_3$, $R_4$=$CH_3$, and n=10–1000, or $R_1$=H, $R_3$=C$(CH_3)_2$—O—C(═O)—NH—$(CH_2)_3$, $R_4$=$CH_3$, and n=10–1000. This compound is suitable for use as a polymerizable wetting agent in a contact lens formulation.

This invention likewise provides a (meth)acrylamide functionalized polyvinylpyrrolidone of the general structure depicted below, which is likewise suitable for use as a polymerizable wetting agent in a contact lens formulation.

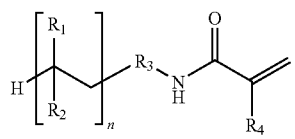

In the formula: $R_1$ is hydrogen or $C_{1-8}$-alkyl; $R_2$ is pyrrolidinone; n=1–10,000; $R_3$ is a divalent aliphatic linkage chain containing up to 8 carbon atoms and up to 2 oxygen, sulfur, and/or nitrogen atoms in the linkage chain, such as S—$(CH_2)_m$ wherein m is 1-6; and $R_4$ is hydrogen or $C_{1-8}$-alkyl, such as $CH_3$. In specific embodiments, $R_1$=H, $R_3$=S—$(CH_2)_m$, "m"=1 to 6, $R_4$=H, and n=10–10,000 or $R_1$=H, $R_3$=S—$(CH_2)_m$, "m"=1 to 3, $R_4$=$CH_3$, and n=10–10,000.

DETAILED DESCRIPTION OF THE INVENTION

The present invention provides methods for preparation of PVP with polymerizable functionalization for use, e.g., as hydrophilic wetting agents in contact lenses. The present invention provides a new class of compositions of matter, comprising functionalized hybrid PDMS/polar amphipathic copolymer block systems. These materials may be used in both industrial and biomedical devices such as components for ophthalmic devices (hydrogels), tissue engineering, transdermal implants, industrial adhesives, sealants, surface protecting agents, etc. For instance, (meth)acrylated PVP derivatives will find effective use in contact lens compositions that contain photopolymerizable components. In practice, during irradiation of the contact lens mix, the (meth)acrylated PVP will polymerize along with the other polymerizable components to provide a non-leachable lens.

As illustrated in detail herein below, their synthesis may involve preparing a PDMS free radical macroinitiator followed by polymerization in the presence of N-vinyl pyrrolidone or other polar vinyl or acrylic monomers susceptible to free radical polymerization in the presence of a CTA (chain transfer agent) such as IPA, isopropoxyethanol or mercaptoethanol to generate the OH— functionalized polymer. The resulting polymer may be methacrylated using different chemistries by reacting the OH group with methacryloyl chloride or Methacrylic anhydride in the presence of a base or alternatively by reaction with isocyanatoethyl methacrylate.

Using this approach a variety of methacrylate (MA) functionalized PDMS-polar copolymer blocks can be synthesized. Examples of materials of interest are PDMS-PVP-MAA and PDMS-polyNIPAAm-MA. The chemistry may also be extended to prepare difunctional methacrylate functionalized triblock copolymers such as MA-PVP-PDMS-PVP-MA and other polymers, starting with commercially available dihydroxy- or diamino-functionalized polydimethylsiloxanes. Persons skilled in the art are familiar in general with the production of block copolymers having functionally active endgroups. For instance, U.S. Pat. No. 5,589,563 (Polymer Technology Group), the disclosure of which is herein incorporated by reference, discloses how to make and use functionalized copolymers.

EXAMPLES

Example 1

(Meth)Acrylated PVP Polymers

The synthesis of meth(acrylate) functionalized PVP is achieved by a methacrylation reaction of hydroxy functionalized PVP that is prepared using reactions known to those skilled in the art. The general structure of polymerizable (meth)acrylated PVP may have, for instance, the following formula:

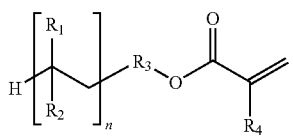

$R_1 = H$; $R_2 = $ pyrrolidinone,
$R_3 = C(CH_3)_2 — O — CH_2 — CH_2$, $C(CH_3)_2$, or $S — (CH_2)_3$,
$C(CH_3)_2 — O — C(=O) — NH — (CH_2)_3$;
$R_4 = H$ or $CH_3$; $n = 1$-$1000$ The first step toward the synthesis of (meth)acrylated PVP copolymers is the polymerization of distilled N-vinyl-2-pyrrolidone using azo initiators such as azobis(isobutyronitrile) (AIBN) and the like in the presence of chain transfer agents such as isopropanol, mercaptoethanol, isopropoxyethanol with or without a solvent to generate hydroxyl terminated PVP of different MW's between 10,000 to 1,000,000 daltons. The resulting hydroxyl terminated PVP is converted to a terminal methacrylate derivative using either methacryloyl chloride, methacrylic anhydride, or isocyanatoethyl methacrylate. One example of this embodiment is synthesized using protocol shown in Scheme 1.

Scheme 1: Synthesis of methacrylated PVP polymer.

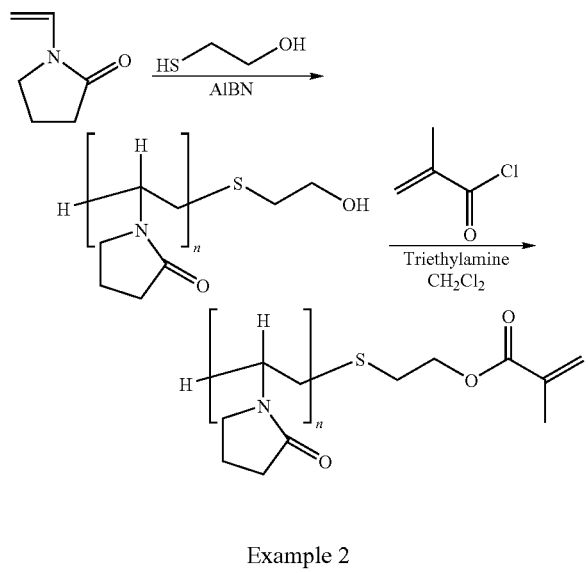

Example 2

(Meth)Acrylamide Functionalized PVP Polymers

Another class of polymerizable PVP is depicted below, wherein the polymerizable functionalization is a (meth)acrylamide group.

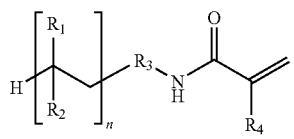

$R_1 = H$; $R_2 = $ pyrrolidinone,
$R_3 = S — (CH_2)_m$, $m = 1$-$6$
$R_4 = H$ or $CH_3$; $n = 1$-$1000$ The first step toward the synthesis of (meth)acrylamide functionalized PVP copolymers is the polymerization of distilled N-vinylpyrrolidone using azo initiators such as azobis(isobutyronitrile) (AIBN) and the like in the presence of an aminoalkylmercaptan chain transfer agent with or without a solvent to generate amino terminated PVP of different MW's between 10,000 to 1,000,000 daltons. The resulting amino terminated PVP is converted to a terminal (meth)acrylamide derivative by reaction with methacryloyl chloride, or methacrylic anhydride. One example of this embodiment is synthesized using protocol illustrated in Scheme 2.

Scheme 2: Synthesis of acrylamide terminated PVP polymer.

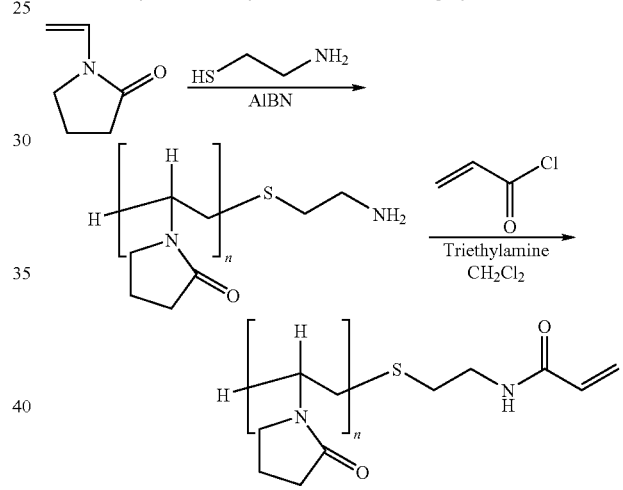

Example 3

Amphipathic Diblock Copolymers Including PDMS-PVP Copolymers

The present invention also provides methods for preparation of novel polydimethylsiloxane (PDMS)—PVP copolymers and other amphipathic copolymers of the general structure depicted in the following formula.

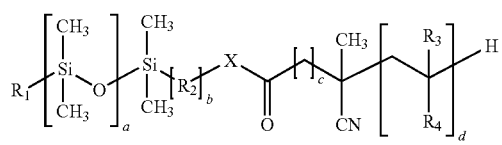

$R_1 = $ alkyl, alkoxy; $R_2 = (CH_2)n$; $(CH_2)m — O(CH_2)n$, m and n can be between 1-16;
$a = 1$-$200$; $b = 1$-$6$; $c = 1$-$6$; $d = 1$-$1000$; $X = O$, $NH$, $S$; $R_3 = H$, $CH_3$;
$R_4 = $ pyrrolidinone, $C(=O)OH$, $C(=O)OAlkyl$, Ph, substituted Ph,
$C(=O)NH_2$, $C(=O)N(alkyl)_2$, $OC(=O)CH_3$, $OH$,
$C(=O)$-oxylethylphosphorycholine A retrosynthetic process for the preparation of the above class of matter is depicted in the following reaction scheme:

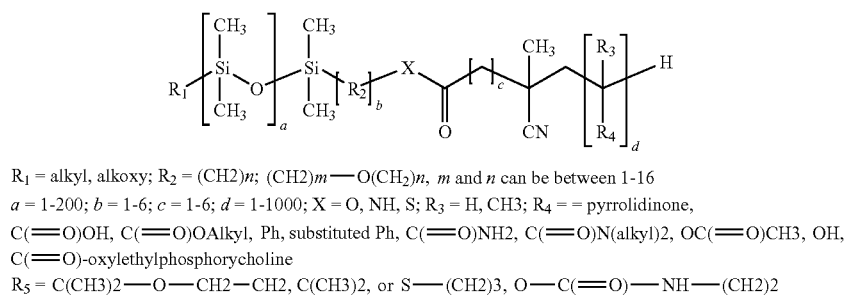

$R_1$ = alkyl, alkoxy; $R_2$ = (CH2)$n$; (CH2)$m$—O(CH$_2$)$n$, $m$ and $n$ can be between 1-16
$a$ = 1-200; $b$ = 1-6; $c$ = 1-6; $d$ = 1-1000; X = O, NH, S; $R_3$ = H, CH3; $R_4$ = = pyrrolidinone,
C(=O)OH, C(=O)OAlkyl, Ph, substituted Ph, C(=O)NH2, C(=O)N(alkyl)2, OC(=O)CH3, OH,
C(=O)-oxylethylphosphorycholine
$R_5$ = C(CH3)2—O—CH2—CH2, C(CH3)2, or S—(CH2)3, O—C(=O)—NH—(CH2)2

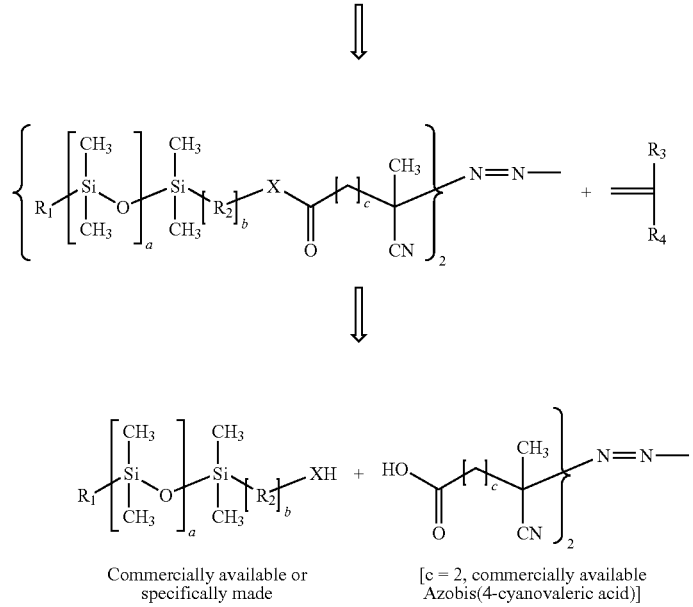

Commercially available or specifically made

[c = 2, commercially available Azobis(4-cyanovaleric acid)]

Example 4

Amphipathic Triblock Copolymers Including PVP-PDMS-PVP Copolymers

The synthetic methodology provided by the present invention also allows synthesis of novel PVP-PDMS-PVP triblock copolymers and other amphipathic copolymers of the general structure depicted in the following formula:

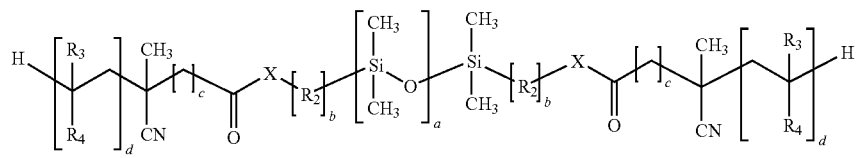

$R_2$ = (CH2)$n$; (CH2)$m$—O(CH2)$n$, m and n can be between 1-16;
$a$ = 1-200; b = 1-6; c = 1-6; d = 1-10000; X = O, NH, S, $R_3$ = H, CH3; $R_4$ = pyrrolidinone,
C(=O)OH, C(=O)OAlkyl, Ph, substituted Ph, C(=O)NH2, C(=O)N(alkyl)2,
OC(=O)CH3, OH, C(=O)-oxylethylphosphorycholine A retrosynthetic approach for the preparation of the above class of matter is depicted in the following reaction scheme, which like that in Example 3 shows the final product preceded by the intermediates which provide it preceded by the starting materials.

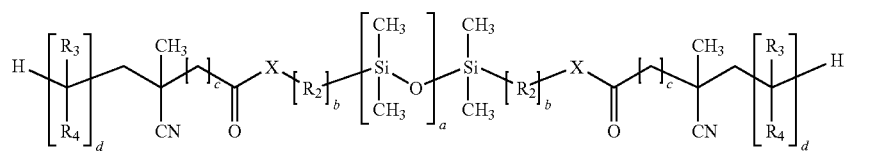

$R_2 = (CH_2)n; (CH_2)m—O(CH_2)n$, m and n can be between 1-16
$a = 1\text{-}200; b = 1\text{-}6; c = 1\text{-}6; d = 1\text{-}1000; X = O, NH, S; R_3 = H, CH_3; R_4 = $ = pyrrolidinone,
$C(=O)OH, C(=O)OAlkyl, Ph,$ substituted $Ph, C(=O)NH2, C(=O)N(alkyl)2, OC(=O)CH3, OH,$
$C(=O)$-oxylethylphosphorycholine

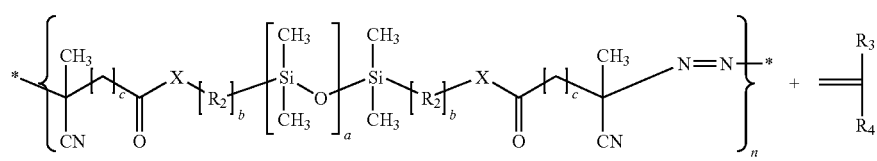

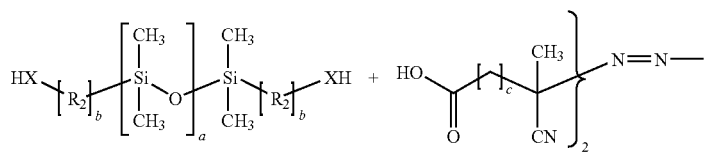

Commercially available or specifically made      [c = 2, commercially available Azobis(4-cyanovaleric acid)]

Example 5

Monofunctional Polymerizable Amphipathic Copolymers Including PDMS-PVP Methacrylate Copolymers Another embodiment of the invention is general class of compounds bearing polymerizable functionality as depicted in the following formula:

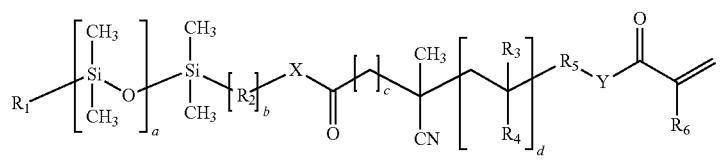

$R_1 = $ alkyl, alkoxy; $R_2 = (CH_2)n; (CH_2)m—O(CH_2)n$, m and n can be between 1-16;
$a = 1\text{-}200; b = 1\text{-}6; c = 1\text{-}6; d = 1\text{-}10000; X = O, NH, S; Y = O, NH;$
$R_3 = H, CH_3; R_4 = $ pyrrolidinone, $C(=O)OH, C(=O)OAlkyl, Ph,$ substituted $Ph, C(=O)NH2,$
$C(=O)N(alkyl)2, OC(=O)CH3, OH, C(=O)$-oxylethylphosphorycholine;
$R_5 = C(CH_3)_2—O—CH_2—CH_2, C(CH_3)_2, S—(CH_2)_2, C(CH_3)_2—O—C(=O)—NH—(CH_2)_2,$
$C(CH_3)_2—O—CH_2—CH_2—O—C(=O)—NH—(CH_2)_2, S—(CH_2)_2—O—C(=O)—NH—(CH_2)_2;$
$R_6 = $ H or CH3

A retrosynthetic approach for the preparation of the above class of matter is depicted in Scheme 5.

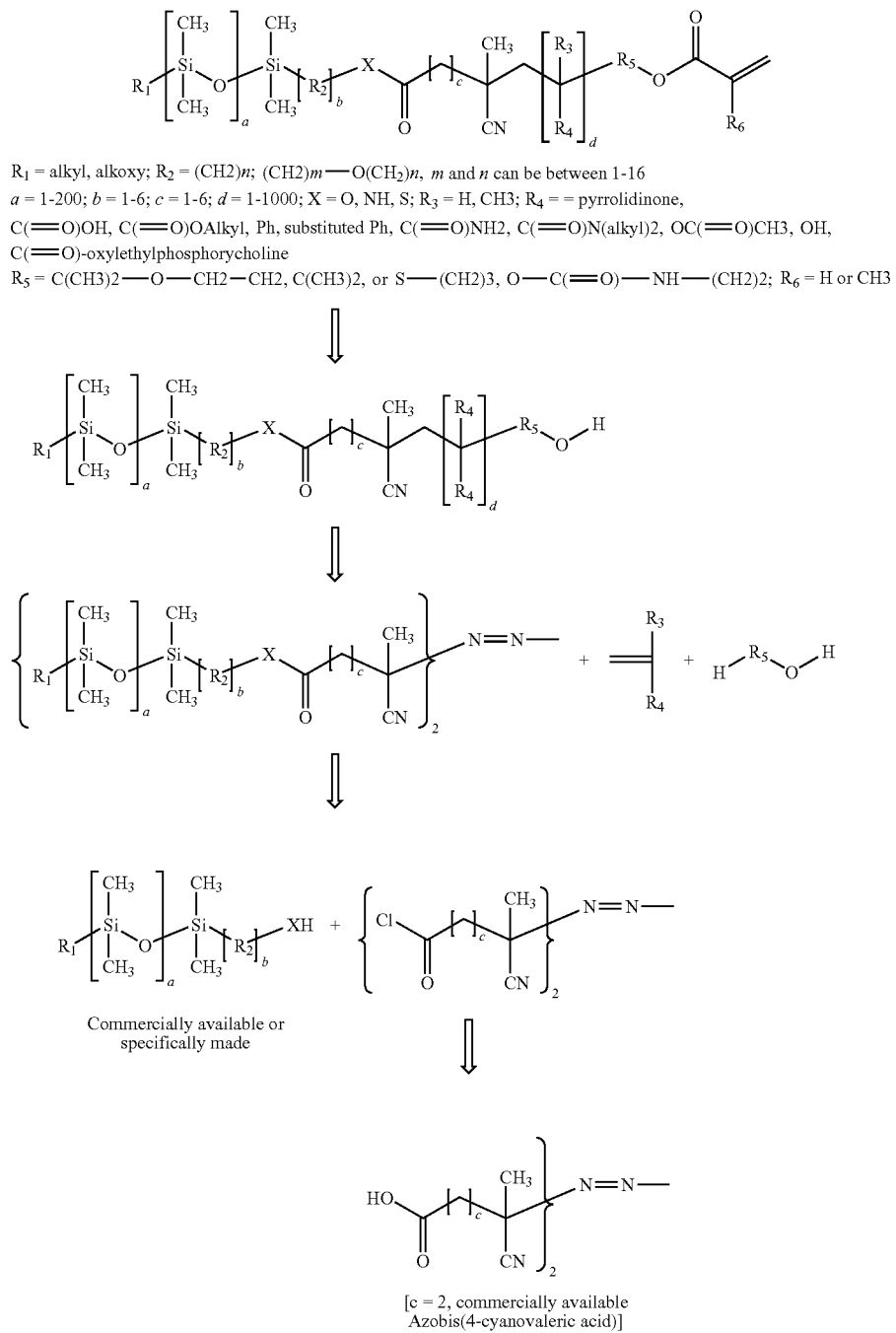

$R_1$ = alkyl, alkoxy; $R_2$ = $(CH2)n$; $(CH2)m$—$O(CH_2)n$, $m$ and $n$ can be between 1-16
$a$ = 1-200; $b$ = 1-6; $c$ = 1-6; $d$ = 1-1000; X = O, NH, S; $R_3$ = H, CH3; $R_4$ = = pyrrolidinone,
C(=O)OH, C(=O)OAlkyl, Ph, substituted Ph, C(=O)NH2, C(=O)N(alkyl)2, OC(=O)CH3, OH,
C(=O)-oxylethylphosphorycholine
$R_5$ = C(CH3)2—O—CH2—CH2, C(CH3)2, or S—(CH2)3, O—C(=O)—NH—(CH2)2; $R_6$ = H or CH3

[c = 2, commercially available Azobis(4-cyanovaleric acid)]

As disclosed above, compositions of matter provided by the present invention may be used—among other things—to make silicone hydrogel contact lenses. Persons skilled in the art are well aware in general of methods of manufacturing such contact lenses. Reference is made, for instance, to U.S. Pat. No. 7,268,198 B2 (Bausch & Lomb), entitled SILICONE HYDROGEL CONTACT LENSES; to U.S. Pat. No. 6,861,123 B2, (Johnson & Johnson), entitled SILICONE HYDROGEL CONTACT LENS; and to U.S. Pat. No. 5,260,000 (Bausch & Lomb), entitled PROCESS FOR MAKING SILICONE CONTAINING HYDROGEL LENSES.

The invention being thus described generically and with reference to specific embodiments, it will be readily apparent to those skilled in the art that the same may be varied in many ways. All such variations are encompassed by the spirit of the invention, the patented scope of which is demarcated in the appended claims.

What is claimed is:

1. An amphipathic diblock copolymer compound having the following structure:

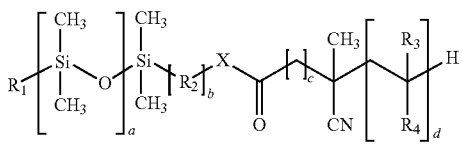

wherein
R$_1$ is alkyl or alkoxy,
R$_2$ is (CH$_2$)$_n$ or (CH$_2$)$_m$—O—(CH$_2$)$_n$ wherein m and n range from 1 to 16,
a is 1 to 200,
b is 1 to 6,
c is 1 to 16,
d is 1 to 10,000,
X is O, NH, or S,
R$_3$ is H or CH$_3$, and
R$_4$ is pyrrolidinone.

2. The amphipathic diblock copolymer of claim 1, formulated for use as a lens care component for contact lenses.

3. The amphipathic diblock copolymer of claim 2, wherein said contact lenses are silicone hydrogel lenses.

4. The amphipathic diblock copolymer of claim 1, formulated for use as an oxygen permeable and wettable backing material for a wound healing device.

5. The amphipathic diblock copolymer of claim 1, formulated for use as a scaffold for tissue engineering.

6. The amphipathic diblock copolymer of claim 1, formulated for use as a component for controlled drug release.

7. The compound of claim 1, wherein R$_1$=butyl; "a" is from 2 to 50; R$_2$=(CH$_2$)$_3$; "b"=1; X=O; R$_3$=H; R$_4$=pyrrolidinone; and "d"=10-10,000.

8. The compound of claim 1, wherein R$_1$=butyl; "a" is from 2 to 50; R$_2$=(CH$_2$)$_3$—O—(CH$_2$)$_2$; "b"=1; X=O; R$_3$=H; R$_4$=pyrrolidinone; and "d"=10-10,000.

9. The compound of claim 1, wherein R$_1$=butyl; "a" is from 2 to 50; R$_2$=(CH$_2$)$_3$; "b"=1; X=NH; R$_3$=H; R$_4$=pyrrolidinone; and "d"=10-10,000.

* * * * *